US008655430B2

(12) United States Patent
Chou et al.

(10) Patent No.: US 8,655,430 B2
(45) Date of Patent: Feb. 18, 2014

(54) POSITIONING SYSTEM FOR THERMAL THERAPY

(75) Inventors: Shih Chin Chou, Miaoli County (TW); Ming Rou Lee, Yilan County (TW); Hsu Chang, Miaoli County (TW); Ching Yao, San Mateo, CA (US)

(73) Assignee: National Health Research Institutes, Mialoi County (TW)

( * ) Notice: Subject to any disclaimer, the term of this patent is extended or adjusted under 35 U.S.C. 154(b) by 1212 days.

(21) Appl. No.: 12/342,450

(22) Filed: Dec. 23, 2008

(65) Prior Publication Data

US 2009/0171185 A1 Jul. 2, 2009

Related U.S. Application Data

(60) Provisional application No. 61/016,659, filed on Dec. 26, 2007.

(51) Int. Cl.
*A61B 5/055* (2006.01)

(52) U.S. Cl.
USPC ............ 600/417; 600/407; 600/410; 600/411

(58) Field of Classification Search
USPC .......... 600/410–411, 417, 421, 425, 427, 429
See application file for complete search history.

(56) References Cited

U.S. PATENT DOCUMENTS

| | | | |
|---|---|---|---|
| 5,147,372 A | 9/1992 | Nymark et al. | |
| 5,242,455 A * | 9/1993 | Skeens et al. | 606/130 |
| 5,280,427 A | 1/1994 | Magnusson et al. | |
| 5,369,679 A | 11/1994 | Sliski et al. | |
| 5,417,210 A * | 5/1995 | Funda et al. | 600/425 |
| 5,722,411 A | 3/1998 | Suzuki et al. | |
| 5,897,495 A | 4/1999 | Aida et al. | |
| 5,938,600 A | 8/1999 | Van Vaals et al. | |
| 5,944,663 A * | 8/1999 | Kuth et al. | 600/411 |
| 6,110,112 A | 8/2000 | Heywang-Koebrunner | |
| 6,206,890 B1 * | 3/2001 | Truwit | 606/130 |
| 6,454,713 B1 | 9/2002 | Ishibashi et al. | |
| 6,514,220 B2 * | 2/2003 | Melton et al. | 601/2 |
| 6,665,554 B1 * | 12/2003 | Charles et al. | 600/427 |
| 7,773,408 B2 | 8/2010 | Takenaga et al. | |
| 2003/0181806 A1 | 9/2003 | Medan et al. | |
| 2004/0199072 A1 * | 10/2004 | Sprouse et al. | 600/424 |
| 2007/0016014 A1 | 1/2007 | Hara et al. | |
| 2007/0239062 A1 | 10/2007 | Chopra et al. | |
| 2007/0282192 A1 | 12/2007 | Rezzonico et al. | |

FOREIGN PATENT DOCUMENTS

| | | |
|---|---|---|
| EP | 1854508 | 11/2007 |
| WO | 00/28882 | 5/2000 |
| WO | WO 2006/123273 | 11/2006 |

* cited by examiner

*Primary Examiner* — Peter Luong
(74) *Attorney, Agent, or Firm* — Occhiuti & Rohlicek LLP

(57) ABSTRACT

Systems and methods are provided for positioning a therapeutic device relative to a target displaced on a platform. A base member has a first track extending along a length of the platform for defining a first pathway for translating the therapeutic device relative to the target. A curved frame is slidably mounted on the base member through the first track. The curved frame has a second track along an interior wall of the curved frame for defining a second pathway for translating the therapeutic device relative to the target. A housing is disposed in the second track of the curved frame and configured to receive the therapeutic device. The housing is extendible at least along a radial direction of the curved frame for defining a third pathway for translating the therapeutic device relative to the target. Applications of the systems and methods may include image-guided thermal therapy.

25 Claims, 4 Drawing Sheets

POSITIONING SYSTEM FOR THERMAL THERAPY

CROSS-REFERENCE TO RELATED APPLICATIONS

This application claims the benefit of U.S. Provisional Application No. 61/016,659, titled "MRI guided thermal therapy system," filed Dec. 26, 2007, the contents of which are incorporated herein by reference.

BACKGROUND

This application relates to positioning systems, for example, positioning systems for thermal therapy.

Thermal therapy makes use of heating techniques, for example, for treating cancers and tissue anomalies. One form of thermal therapy, for example, uses high intensity focused ultrasound (HIFU). By inducing local heating, HIFU can cause irreversible tissue necrosis rapidly, e.g., within a few seconds.

For a thermal therapy procedure to be both safe and effective, the amount of energy delivered to a patient, for example, through an energy transducer, is preferably controlled. The focus of energy application may also be controlled to direct energy only into intended regions while leaving surrounding healthy tissue undamaged. This can be done, for example, by adjusting the location of the energy transducer using a positioning system.

In some thermal therapy systems, imaging devices (e.g., magnetic resonance imaging systems (MRI) and computed tomography (CT) systems) are used in conjunction with the energy transducer to provide image guidance in real time. The duration, intensity, and location of energy application can be respectively determined, for example, by estimating the degree of tissue necrosis in a diseased region through MRI-based temperature measurements.

SUMMARY

In one aspect, in general, a system is provided for positioning a therapeutic device relative to a target displaced on a platform. A base member has a first track extending along a length of the platform for defining a first pathway for translating the therapeutic device relative to the target. A curved frame is slidably mounted on the base member through the first track. The curved frame has a second track along an interior wall of the curved frame for defining a second pathway for translating the therapeutic device relative to the target. A housing is disposed in the second track of the curved frame and configured to receive the therapeutic device. The housing is extendible at least along a radial direction of the curved frame for defining a third pathway for translating the therapeutic device relative to the target.

Embodiments of this system may have one or more of the following features.

The therapeutic device may include an ultrasound transducer, or alternatively, a biopsy needle.

The housing may include a means for pivoting the therapeutic device to enable rotation of the therapeutic device about one or more of three orthogonal axes.

An actuator may be coupled to the housing and configured to receive one or more control signals for actuating the housing. A second actuator may be coupled to the curved frame and configured to receive a control signal for actuating the housing. A third actuator may be coupled to the first track and configured to receive a control signal for actuating the curved frame.

The therapeutic device may include an energy transducer configured to direct a signal at a selected region of the target for inducing thermal effect. The signal directed at the selected region of the target may include a spatial energy field.

An imaging device may be provided for obtaining information characterizing a degree of the induced thermal effect at the selected region of the target.

In addition, a processor may be provided for receiving and processing the information obtained by the imaging device to generate the control signal(s) for actuating the housing and/or the curved frame. The processor may be further configured to generate the control signal by comparing the degree of the induced thermal effect with a desired thermal effect.

The processor may include a control module coupled to the energy transducer. The control module may be configured to generate a second control signal for controlling a characteristic of the signal of the energy transducer based on the information obtained by the imaging device. The characteristic of the signal may include a magnitude and/or duration of the signal.

In some examples, the energy transducer may include an array of energy-transducing elements, each element configured to generate a respective component of the signal of the energy transducer. The control module may be further configured to generate a third control signal for controlling a respective frequency of each of the respective components of the signal. Additionally, the control module may be configured to generate a fourth control signal for controlling a respective phase of each of the respective components of the signal.

The imaging device may be an MRI (magnetic resonance imaging), or alternatively, a CT (computed tomography) system.

The base member may be mechanically coupled, for example, fixed or movably coupled to the platform. It may include a first base member and a second base member substantially parallel to the first base member, each having a respective track extending along the length of the platform.

In some examples, the base member may further include a sheet (or mat) that can be translated relative to the platform. The sheet can be configured to receive MRI receiver coils.

In another aspect, in general, a method is provided for positioning a therapeutic device relative to a target displaced on a platform. The therapeutic device is configured to induce a therapeutic effect at a selected region of the target. The method includes detecting information characterizing a degree of the therapeutic effect at the selected region of the target; processing the detected information to determine a desired location of the therapeutic device relative to the target; and generating a signal for a positioner coupled to the therapeutic device for directing the therapeutic device to the desired location, including translating the therapeutic device in one or more of a predefined set of pathways. The predefined set of pathways includes a first pathway for translating the therapeutic device along a length of the platform; a second pathway for translating the therapeutic device along a curved path in a plane substantially perpendicular to the first pathway; and a third pathway for translating the therapeutic device along a radial axis of the curved path.

Embodiments of this method may have one or more of the following features.

Detecting information characterizing a degree of the therapeutic effect may include generating a medical image of the selected region of the target. The medical image may include an MR image or a CT image.

Processing the detected information may include comparing the degree of the therapeutic effect with a desired therapeutic effect.

The therapeutic device may include an ultrasound transducer, and the therapeutic effect may include a thermal effect.

The method may further include rotating the therapeutic device about one or more of three orthogonal axes.

In another aspect, in general, an apparatus is provided for image-guided therapy. An imaging system includes a platform for supporting a target and for translating the target to a desired location. The platform is movable relative to the imaging system. A positioning system is coupled to the platform and configured for positioning a therapeutic device relative to the target on the platform. The positioning system includes a base member mechanically coupled to the platform. The base member has a first track extending along a length of the platform. A curved frame is slidably mounted on the base member through the first track, the curved frame having a second track along an interior wall of the curved frame. A housing is disposed in the second track of the curved frame and configured to receive the therapeutic device, the housing being extendible at least along a radial direction of the curved frame.

Embodiments of this apparatus may have one or more of the following features.

A first control system may be coupled to the imaging system and configured to provide a first control signal for moving the platform relative to a stationary imaging system, e.g., a magnet.

A second control system may be coupled to the positioning system and configured to provide a second control signal for controlling the positioning system to move the therapeutic device relative to the target.

The second control system may include a processor for receiving an image of the patient generated by the imaging system and for processing the image to determine a degree of an effect of the therapy. The processor may be further configured to compare the degree of the effect of the therapy with a desired result and to generate the second control signal for controlling the positioning system based on a result of the comparison.

The therapeutic device includes an ultrasound transducer.

The imaging system may include an MRI device.

Various embodiments of the aspects described above may include one or more of the following advantages.

In some embodiments where the therapeutic device (e.g., ultrasound transducer) is to be used in conjunction with one or more imaging system, the system for positioning the therapeutic device is configured in a curved shape suitable to fit inside the main structure of the imaging system (such as a ring-shaped gantry of MRI or CT scanner). In some examples, because the based member of the system is mechanically coupled to the platform (rather than fixed to the scanner or other structures of the imaging system), the positioning of the therapeutic device relative to the patient body can be controlled without the need to compensate for platform travel, which may be needed, for example, when different segments of the patient body need to be imaged before or during the procedure. Further, the system for positioning the therapeutic device can be configured as a stand-alone system and conveniently integrated with various imaging modalities without having to modify the imaging machine to use. Additionally, the freedom of the platform to be moved relative to the first track (e.g., guide rails) or the base member will allow the patient to be sent to other imaging system such as CT or PET (Positron emission tomography) device for imaging.

Other features and advantages of the invention are apparent from the following description, and from the claims.

DETAILED DESCRIPTION

1 Positioning System

Figure 1:
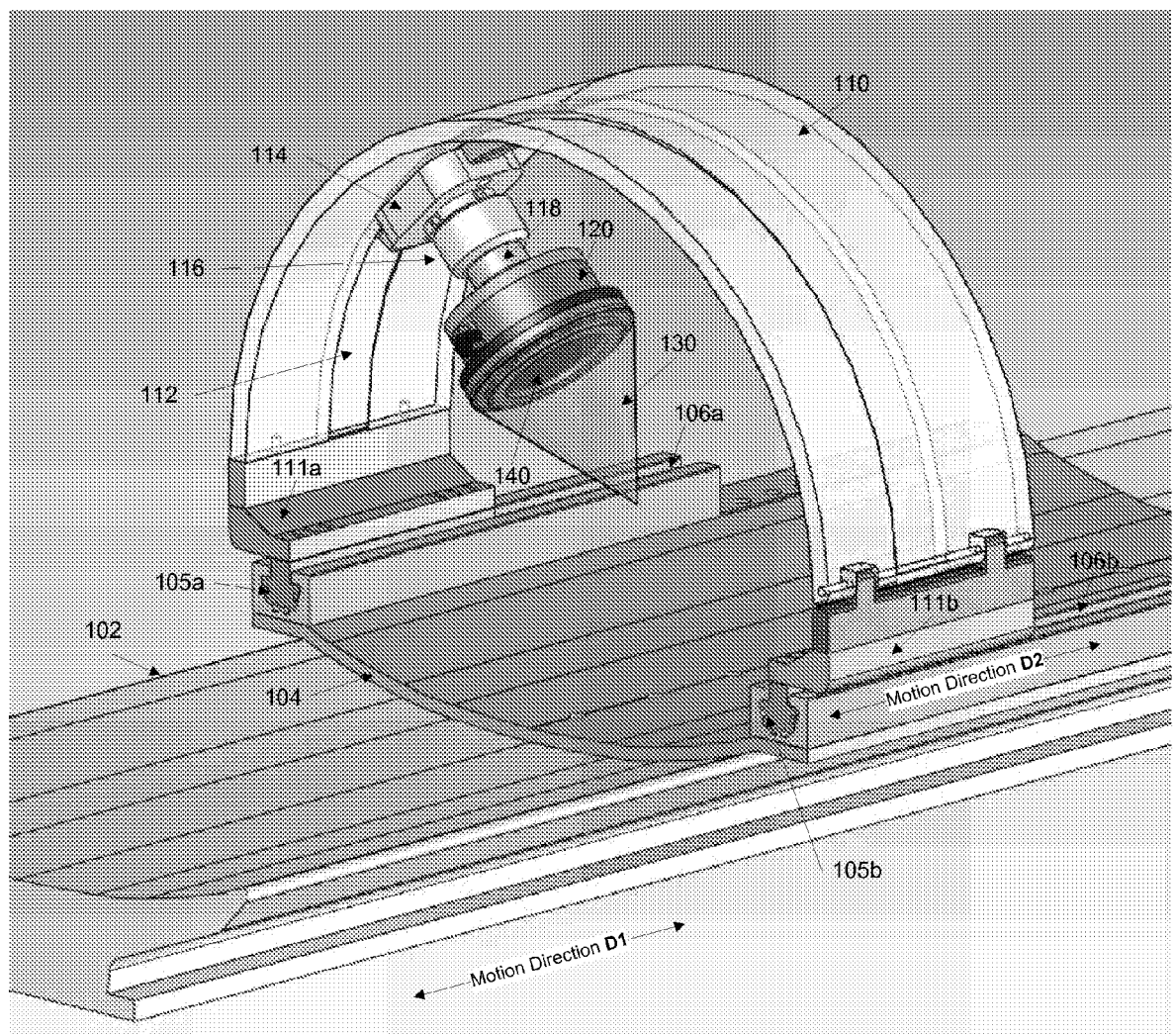
FIG. 1 is an isometric view of one embodiment of a positioning system for use with an energy transducer.

Referring to FIG. 1, one embodiment of a positioning system 100 is provided for positioning an energy transducer 120 (e.g., an ultrasound transducer) configured for performing a thermal procedure on a patient (not shown). The transducer 120 is configured to direct a spatial energy field 130 (e.g., in the form of ultrasound beams) toward a target tissue region within the patient. Each sonication of the beams may treat a defined portion of the target tissue, for example, a small focal area of the beams. The entire target tissue can be treated by moving the transducer 120 to successively apply sonication to each of a sequence of portions of the target tissue, for example, according to a protocol established by a computer program or a physician.

In some examples, a fluid-filled bag 140 may be coupled to (or otherwise positioned against) a surface of the transducer 120 so that, when the transducer 120 is pressed against the patient body, the contents of the bag 140 (e.g., acoustic gel, water, or other fluid) may facilitate acoustic coupling between the transducer 120 and the patient.

To position the transducer 120 at the desired locations for therapy, the positioning system 100 provides a set of mechanical and/or electrical components that may operate together to translate the transducer 120 in linear and/or rotational modes in multiple dimensions as described in detail below.

In this embodiment, the positioning system 100 includes a platform 102 for supporting the patient to be treated. Depending on the nature of the treatment, the patient may lie on the platform 102 either in a prone position (face down), or alternatively, in a supine position (face up). The platform 102 can be translated in a linear manner along its longitudinal axis (referred to herein as D1 as shown in FIG. 1) for moving the patient to a desired location. In some cases where the patient is to be monitored by MRI during the procedure, the platform 102 can be used to place the patient at various locations inside the MRI magnet for imaging.

The positioning system 100 also includes a base member 104 mechanically coupled to the platform 102. In some examples, the base member 104 is secured to the platform 102 and thus follows the movement of the platform 102. The base member 104 has a pair of linear guide rails 106a and 106b in parallel alignment. A curved frame 110 (e.g., an arc-shaped frame) is slidably mounted onto the guide rails 106a and 106b by engaging slide blocks 111a and 111b with guide rails 106a and 106b, respectively. Thus, the curved frame 110 is movable along axis D2 relative to the guide rails 106 and the platform 102.

A housing 114 is mounted onto the curved frame 110 through a rail track 112 along an inner wall of the curved frame 110. The housing 114 is configured to move the transducer 120 in both linear and rotational directions. For example, the housing 114 may include an extension arm 116 extendable along a radial direction of the curved frame 114. The housing 114 may also include a pivoting member 118 (e.g., a swivel) configured for rotating the transducer 120 about one or more of three orthogonal axes.

In some examples, the housing 114 may be coupled to an actuator (not shown) capable of receiving external signals for actuating the housing 114. One example of the actuator is an electric motor, which can be a piezoelectric vibrational motor that may operate within the field of an MRI without producing substantial magnetic interference. The actuator may include a set of position sensors, for example, configured to measure the linear/rotational position of the transducer 120 to provide feedback positioning control.

Using the positioning system 100, the transducer 120 can be translated relative to the patient in various linear and rotational modes, as described in detail below.

A first mode of translation is to move the platform 102 (and therefore the patient) along direction D1. For example, prior to the treatment, the patient may first lie down on the platform 102 outside an MRI gantry and then be moved into the gantry for imaging.

A second mode is to slide the curved frame 110 relative to the guide rails 106 or base member 104 along direction D2. In cases where the guide rails 106 or base member 104 is fixed to the platform 102, sliding the curved frame 110 provides adjustment of the transducer 120 along the longitude axis D2 with respect the patient lying on the platform 102.

Figure 2A:
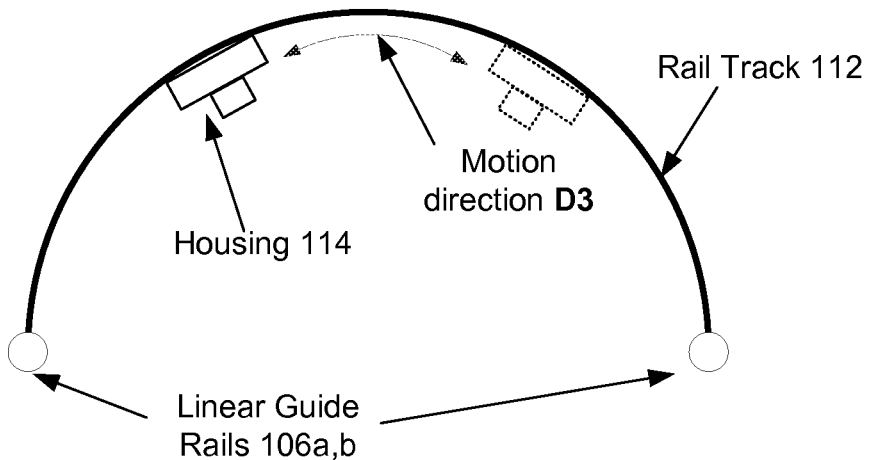
FIGS. 2A-2C are schematic representations of various modes of translation and rotations provided by the positioning system of FIG. 1.

Referring now to FIG. 2A, a third mode of translation is to slide the housing 114 via the rail track 112 along the inner wall of the curved frame 110 (referred to as direction D3).

Figure 2B:
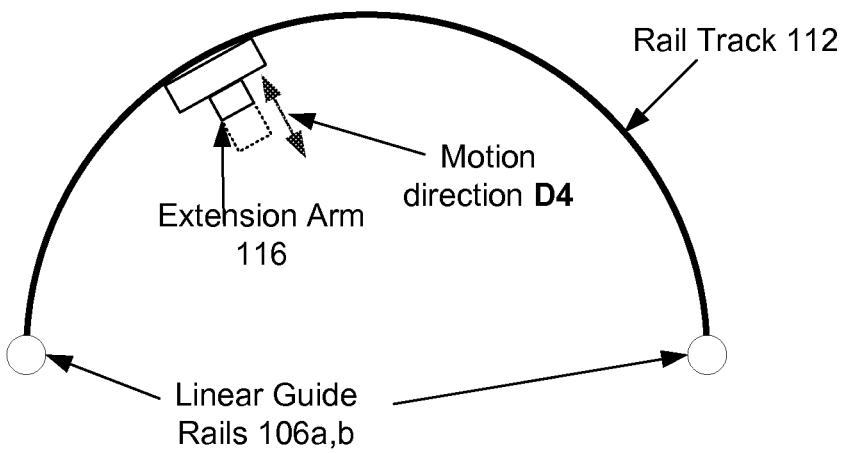

Referring to FIG. 2B, a fourth mode of translation is to extend and contract the extension arm 116 along a radial axis (referred to as direction D4) of the rail track 112. This can provide fine tuning for focusing the ultrasound beams to the desired depth of the treatment region.

Figure 2C:
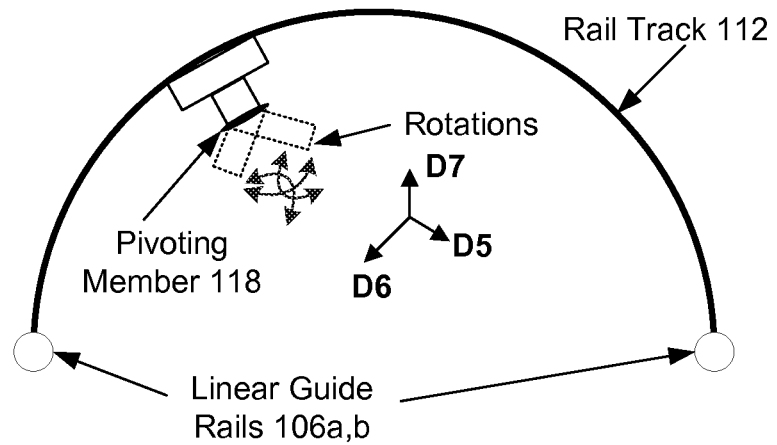

Referring to FIG. 2C, the transducer 120 can be further rotated about each of three orthogonal axes (referred to as D5, D6, and D7) through the pivoting member 118. This can provide roll and pitch control of the transducer 120 so that ultrasound beams can be directed at various angles to reach the desired treatment spot.

Referring again to FIG. 1, in an alternative embodiment of the positioning system 100, the guide rails 106a and 106b are directly mounted to the platform 102 without being coupled to the base member 104. The base member 104 can be used as a mechanically separated piece of mat that may, for example, house MRI receiver coils or registration markers. Moreover, an additional set of sensor and/or actuator may be coupled to one or both of the slide blocks 111a and 111b for receiving control signal for translation.

2 MRI-guided Thermal Therapy

In some examples, the positioning system 100 may be integrated with one or more imaging devices that are configured, for example, to obtain anatomic and physiological information and conditions about the tissue of the patient and/or about the degree of treatment effects. Examples of imaging devices suitable for use here include magnetic resonance imaging (MRI) system and computed tomography (CT) system. When MRI is used during the thermal procedure, for instance, a portion or the entirety of the positioning system 100 may be placed within a magnet (not shown) of an MRI system, which forms a static magnetic field for generating MR images.

Figure 3:
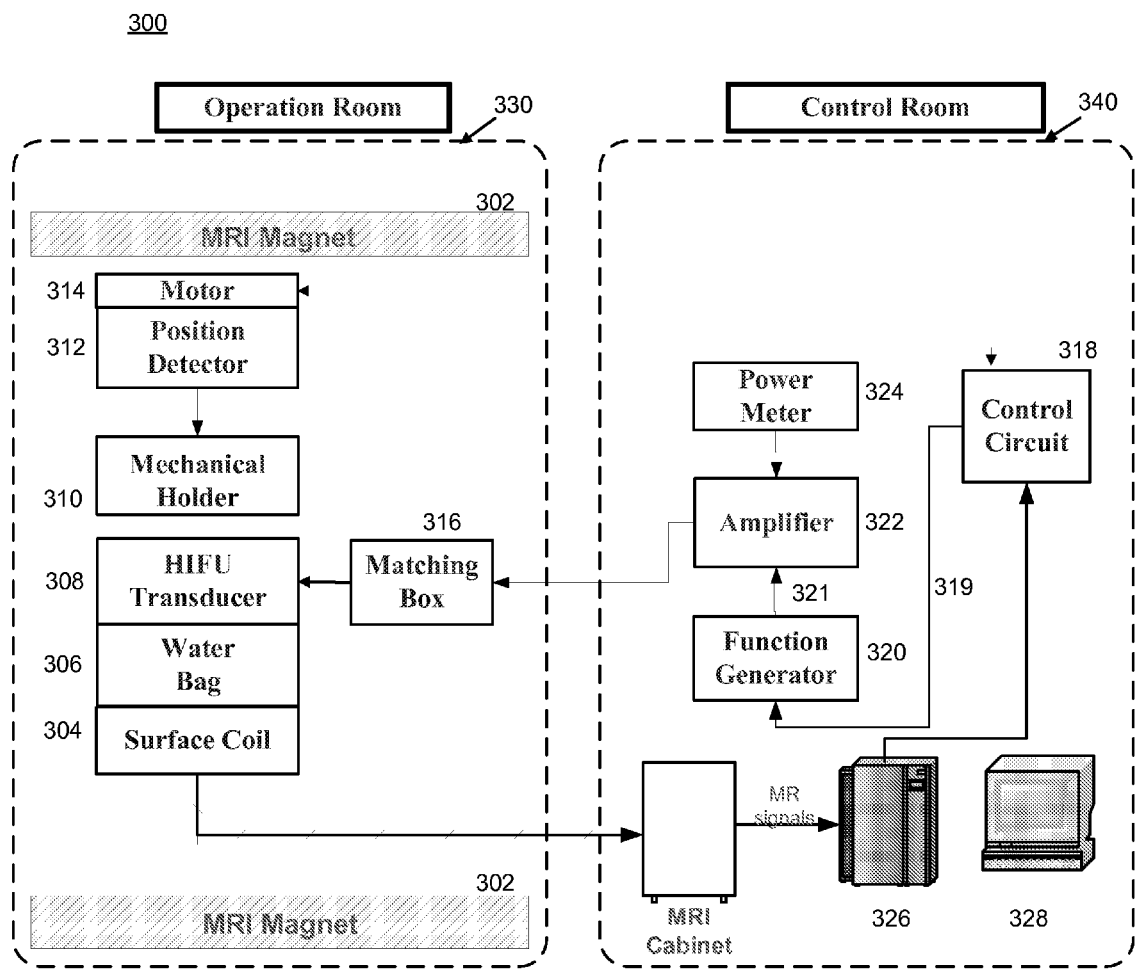
FIG. 3 is a block diagram of one embodiment of an MRI-guided thermal therapy system.

Referring to FIG. 3, one embodiment of an MRI-guided thermal therapy system 300 is shown. Patients are received and treated in an operation room 330. The operation room 330 contains magnet 302 of an MRI system for imaging, a HIFU transducer 308 for directing acoustic beams to the target tissues of a patient, and the positioning system 100 of FIG. 1 for translating the transducer 308 in multiple degrees of freedom to desired locations.

In this embodiment, the positioning system 100 includes a mechanical holder 310 (similar to the housing 114 of FIG. 1) in which the transducer 308 is mounted. The mechanical holder 310 is coupled to one or more motors 314 for actuating the transducer 308. The motor 314 may be a piezoelectric motor operative in the presence of strong magnetic fields, or alternatively, a hydraulic drive system without creating substantial interference with the magnetic fields of the MRI system. A position detector 312 (e.g., linear and/or rotary encoder) is coupled to each of one or more of the motors 314 for converting linear and rotary positions of the transducer 308 into electrical signals for positioning control.

In some examples, the transducer 308 may be a piezoelectric transducer that can convert electrical signals into ultrasonic signals. The power level and the duration of the ultrasonic signals can be modulated by external control signals, for example, activation signals provided by an amplifier 322 through a matching box 316. In other examples, an array transducer (e.g., a 1D or 2D phased array) may be used. In addition to the power level and duration of the ultrasonic signals, the respective frequency and phase of the signal components generated by individual elements of the array may also be controlled.

A water bag 306 is coupled to the transducer 308 for facilitating acoustic transmission when the transducer 308 is pressed against the patient body (e.g., anterior abdominal wall) during treatment. Preferably, the membrane of the water bag 306 is made of materials that are substantially transparent to ultrasound beams, such as mylar, polyvinyl chloride (PVC), polyurethane (PU), or other suitable plastic thin film materials.

In some examples, MRI images of the patient may be taken before or during the treatment for planning and monitoring purposes. For instance, a radio frequency (RF) field may be directed at a tissue to be imaged, inducing proton resonance of the tissue that generates a magnetic resonance (MR) response signal. A surface coil assembly 304 is provided to detect the magnetic resonance signal, which can be used to construct images of the target tissue for analysis. In some examples, the surface coil assembly 304 may be positioned between the water bag 306 and the patient body to improve detection efficiency over a selected region of interest.

In order to reduce electromagnetic interference to the MRI system, a group of control electronics of the therapy system 300 are preferably located away from the magnet 302, for example, in a control room 340 separate from the operation room 330. In some examples, the group of control electronics includes a control circuit 318, a power meter 324, a function generator 320, and an amplifier 322. The control circuit 318 is configured to receive position information of the transducer 308 detected by the position detector 312 and to generate a control signal for the motor 314. The control circuit 318 is also configured to receive instructions from a processor 326, which processes the MR images of the patient to determine, for example, the amount of sonication needed to achieve a desired effect and the position of the treatment spot. Upon receiving instructions from the processor 326, the control circuit 318 sends a signal 319 to the function generator 320 to generate a drive signal 321 that, after amplification by the amplifier 322, is transmitted to the matching box 316 for modulating the acoustic output of the transducer 308. Upon determining that the desired thermal effect is achieved, the processor 326 sends position control signals via the control circuit 318 to the motor set to translate the transducer to the next treatment position.

In some implementations, MRI images of the target tissue region are obtained during the treatment and processed to estimate the degree of thermal effects in the target region and to determine the amount of treatment that remains to be performed.

Figure 4:
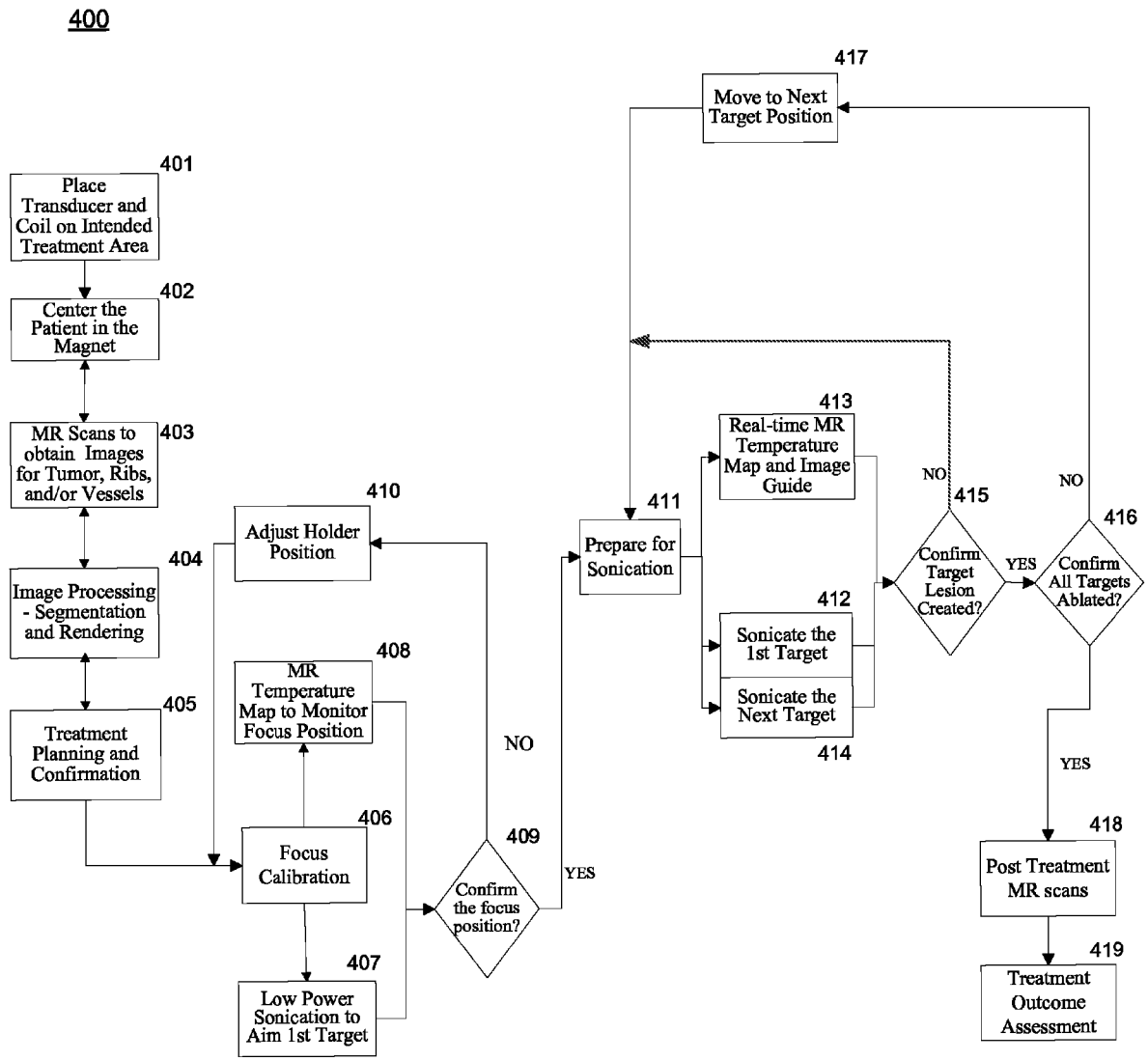
FIG. 4 is a flow chart of a procedure for use with the MRI-guided thermal therapy system of FIG. 3.

Referring now to FIG. 4, an exemplary procedure 400 for use with the MRI-guided thermal therapy system 300 is described in detail below.

At step 401, a patient lies down on the platform 102, and a physician places the transducer 308 and the surface coil 304 over a target region of the patient body (e.g., using the positioning system 100 of FIG. 1).

At step 402, the patient and the transducer 308 is delivered into the magnet 302, for example, by moving the platform 102 into the magnet.

At step 403, the physician performs MR scans on the patient to obtain images of the target area. These images may provide information relating to the patient's anatomic and physiological conditions, such as the size, distribution, and location of the tumor to be ablated as well as physical information about the surrounding healthy tissues, blood vessels, and rib cage structures.

At step 404, these images may be further enhanced using image processing techniques such as segmentation and rendering to highlight tumor tissue from healthy tissue in 2D or 3D visualization.

At step 405, the enhanced MR images as well as other information of the patient are used for determining a treatment plan, for example, with the assistance of a computer program. The treatment plan may include a set of target spots identified for sonication and the detailed procedure for treating each one of the target spots.

At step 406, the thermal therapy system 300 performs a calibration test. The test may determine the initial location of the transducer and the initial parameters for modulating the transducer (in some cases, for respectively modulating the individual elements of an array transducer).

At steps 407 and 408, the system 300 delivers a test sonication at a pre-determined lower energy setting for a short time interval on the first target spot. In the meantime, the MRI system scans the treatment area to obtain MR images, and in some examples, further processes the MR images to estimate the degree of thermal effect induced by the sonication (for example, based on a temperature mapping of the treated spot).

At step 409, the system 300 uses the acquired MR images to determine whether the heated spot coincides with the intended treatment spot. In cases where the heated spot resides outside or partially outside the intended spot, coarse adjustment and/or fine tuning of the transducer's position is performed using the positioning system 100 (at step 410). The test sonication is repeated until the ultrasound beams are accurately focused to the intended spot. The positioning parameters for treating the first target spot are then recorded.

Based on the calibration results, the system 300 performs actual treatment to each of the target spots in the following steps.

At steps 412 and 413, the system applies sonication to the first target spot at a pre-determined power level. MR images of the target spot are acquired for evaluating the degree of thermal effect in real time. Once a desired effect is achieved (e.g., indicated by detection of a predetermined tissue condition such as internal temperature or protein denaturation), the thermal session on the first target spot concludes (at step 415).

At step 416, the transducer is moved to the next position to repeat the thermal procedure. After the last target spot in the treatment plan has been ablated, the system proceeds to a post-treatment stage, at which time MR images of the post-treatment tissue are used for evaluation and assessment.

It is to be understood that the systems and methods described above are intended to illustrate and not to limit the scope of the invention. Various alternative embodiments may be available. Also, the positioning system 100 of FIG. 1 can be used for positioning various therapeutic and/or diagnostic devices besides the energy transducer 120 illustrated in the figure. For example, the housing 114 may be modified to hold a different type of ablation device or a biopsy needle.

For purposes of illustration, in the example of FIG. 1, the actuator is described as being coupled to the housing 114 for actuating the housing 114. In other examples, there may be one or more actuators coupled to the housing 114 and/or other components of the positioning system 100 to facilitate motion control of the therapeutic device. For instance, there may be a set of actuators coupled to the positioning system 100 (including individual modules respectively coupled to the platform 102, the slide blocks 110, the extension arm 116, the pivoting member 118, and possibly other components) such that motion of the therapeutic device in each one of the six degrees of freedom (D1-D6) can be controlled independently. Further, each one of these individual modules may be configured to be electrically/mechanically controlled by external signals.

In some implementations, the mechanical components of the positioning system 100 are made primarily of plastic materials together with some metallic parts. When used in conjunction with MRI systems, the therapeutic devices and the positioning system are configured to be MRI-compatible. When used with other imaging systems (e.g., X-ray or CT devices), even in cases where the therapeutic device and/or the coupled control components (such as motor or actuator) may cause certain interference to the images, image-guided therapy can still be performed by moving the patient in and out of the imaging gantry using the platform.

Other embodiments are within the scope of the following claims.

What is claimed is:

1. An apparatus for providing therapy to a patient, said apparatus comprising a therapeutic device having an energy transducer for directing energy towards a selected region of a target within said patient by causing a spatial energy field to exist in said selected region of said target, said spatial energy field causing said selected region of said target to be heated, a housing for enclosing said therapeutic device, a magnetic resonance imaging system for obtaining information representative of an extent of heating at said selected region of said target, a processing system configured to receive and process said information from said magnetic resonance imaging system, said processing system comprising a control module coupled to said energy transducer and being configured to generate, based at least in part on said information, a control signal for controlling application of said spatial energy field, a platform translatable along a first direction, a base member configured to be mechanically coupled to said platform for supporting said patient, said base member comprising a first track extending along said first direction for defining a first pathway for translating said therapeutic device relative to said target, a curved frame mounted on said base member, said curved frame being mounted to slide along said first pathway, said curved frame having an interior wall that faces said patient, said interior wall having formed thereon a second track that defines a second pathway for translating said therapeutic device relative to said patient, wherein said housing is suspended from said second track and extendable radially inward toward said patient, thereby defining a third pathway for translating said therapeutic device relative to said target, said housing being disposed between said second track and said patient, wherein the base member comprises a mechanically separated piece of mat that can be translated relative to the platform, the mat housing MRI receiver coils.

2. The system of claim 1, wherein the housing includes a pivoting member for pivoting the therapeutic device to enable rotation of the therapeutic device about one or more of three orthogonal axes.

3. The system of claim 1, further comprising an actuator coupled to the housing and configured to receive a control signal for actuating the housing.

4. The system of claim 1, further comprising an imaging device for obtaining information characterizing a degree of the induced thermal effect at the selected region of the target.

5. The system of claim 4, wherein the processing system is configured for receiving and processing the information obtained by the imaging device to generate the control signal for actuating the housing.

6. The system of claim 5, wherein the processing system includes a control module coupled to the energy transducer.

7. The system of claim 6, wherein the control module is configured to generate a second control signal for controlling a characteristic of the signal of the energy transducer based on the information obtained by the imaging device.

8. The system of claim 7, wherein the characteristic of the signal includes a magnitude of the signal.

9. The system of claim 7, wherein the characteristic of the signal includes a duration of the signal.

10. The system of claim 7, wherein the energy transducer includes an array of energy-transducing elements, each element configured to generate a respective component of the signal of the energy transducer.

11. The system of claim 10, wherein the control module is further configured to generate a third control signal for controlling a respective frequency of each of the respective components of the signal.

12. The system of claim 10, wherein the control module is further configured to generated a fourth control signal for controlling a respective phase of each of the respective components of the signal.

13. The system of claim 4, wherein the processing system is configured to generate the control signal by comparing the degree of the induced thermal effect with a desired thermal effect.

14. The system of claim 1, wherein the base member includes a first base member and a second base member substantially parallel to the first base member, each base member having a respective track extending along the length of the platform.

15. The system of claim 1, wherein the base member is fixed to the platform.

16. The system of claim 1, wherein the therapeutic device includes an ultrasound transducer.

17. The system of claim 1, wherein the base member is mechanically coupled to the platform.

18. The system of claim 1, wherein the base member further includes a sheet that can be translated relative to the platform.

19. The system of claim 1, wherein the housing extends toward the patient in a radial direction.

20. A method for positioning a therapeutic device relative to a target within a patient displaced on a platform, said therapeutic device being configured to heat a selected region of said target, said method comprising directing energy from a therapeutic device towards said selected region of said target, thereby causing a spatial energy field that results in heating of said selected region of the target, detecting information characterizing a degree of said therapeutic effect at said selected region of the target, wherein detecting information characterizing a degree of the therapeutic effect at said selected region of said target includes generating a magnetic resonance image of said target, wherein generating said magnetic resonance image comprises receiving a signal from MRI receiver coils housed by a mechanically separated piece of mat under said patient, said mat being translatable relative to said platform, processing said detected information to determine a desired location of said therapeutic device relative to the target, generating a signal for a positioner coupled to said therapeutic device for directing said therapeutic device to said desired location, in response to said signal, translating said therapeutic device in one or more of a predefined set of pathways, wherein said predefined set of pathways includes a first pathway for translating said therapeutic device along a length of said platform, a second pathway for translating said therapeutic device along a curved path, under which said therapeutic device is suspended, in a plane substantially perpendicular to said first pathway, and a third pathway for translating said therapeutic device along a radial axis of said curved path under which said therapeutic device is suspended.

21. The method of claim 20, wherein detecting information characterizing a degree of the therapeutic effect includes generating a medical image of the selected region of the target.

22. The method of claim 20, wherein processing the detected information includes comparing the degree of the therapeutic effect with a desired therapeutic effect.

23. The method of claim 20, wherein the therapeutic device includes an ultrasound transducer.

24. The method of claim 20, further comprising rotating the therapeutic device about one or more of three orthogonal axes.

25. The method of claim 20, further comprising pivoting the therapeutic device to enable rotation of the therapeutic device about one or more of three orthogonal axes.

* * * * *